United States Patent [19]

Gill

[11] 4,085,795
[45] Apr. 25, 1978

[54] METHOD FOR USING GEOTHERMAL ENERGY

[76] Inventor: George Herbert Gill, 1817 W. 21st St., Joplin, Mo. 64801

[21] Appl. No.: 684,611

[22] Filed: May 10, 1976

[51] Int. Cl.² .......................... F28D 15/00; B01J 8/00
[52] U.S. Cl. ...................................... 165/45; 60/641; 23/288 K
[58] Field of Search .......................... 165/45; 60/641; 23/288 K

[56] References Cited

U.S. PATENT DOCUMENTS

| | | | |
|---|---|---|---|
| 3,751,228 | 8/1973 | Semenov | 23/288 K UX |
| 3,805,885 | 4/1974 | Van Huisen | 165/45 |
| 3,858,397 | 1/1975 | Jacoby | 165/45 X |
| 3,874,174 | 4/1975 | Greene | 165/45 X |
| 3,901,659 | 8/1975 | Joklik et al. | 23/288 K |
| 3,935,102 | 1/1976 | Swearingen | 165/45 X |
| 3,975,912 | 8/1976 | Greene | 165/45 X |
| 3,986,362 | 10/1976 | Baciu | 60/641 |

Primary Examiner—Charles J. Myhre
Assistant Examiner—Ira S. Lazarus
Attorney, Agent, or Firm—R. S. Sciascia; Roy Miller

[57] ABSTRACT

Geothermal energy is used to provide the temperatures and pressure necessary for catalytic conversion of carbon monoxide and hydrogen to methanol by lowering the reaction chamber into a geothermal well or by otherwise using geothermal fluids to supply heat and pressure to the reaction chamber.

2 Claims, 4 Drawing Figures

4,085,795

METHOD FOR USING GEOTHERMAL ENERGY

STATEMENT OF GOVERNMENT INTEREST

The invention described herein may be manufactured and used by or for the Government of the United States of America for governmental purposes without the payment of any royalties thereon or therefor.

BACKGROUND OF THE INVENTION

The present invention relates to a method for using geothermal energy, and more particularly to a method for the catalytic conversion of carbon monoxide and hydrogen to methanol.

Geothermal energy, the heat from rocks or fluids within the earth's crust, is only available in certain localities, quite often remote from cities or other potential users of this energy. At present the only way of transporting this energy is by converting it to electricity and transmitting the electrical energy to the use area. Also, many sources of geothermal energy present problems in that the liquid or gas from geothermal wells is highly corrosive and cannot be used in turbines without going through an intermediate heat exchanger or a cleaning process.

SUMMARY OF THE INVENTION

Accordingly, the present invention provides a method for converting this geothermal energy into a more useful form, such as a liquid fuel or the like, so it can be stored and shipped easily for use in other locations. A chemical reaction vessel, made of a corrosion resistant material, is placed in a geothermal well, or in the effluent therefrom. The reaction vessel has an input and a discharge pipe to flow the reactants through a catalyst in the reaction vessel. The fluid in the well is circulated, if necessary, for better energy flow and temperature control.

The advantages and novel features of the present invention will become apparent from the following detailed description when considered in conjunction with the accompanying drawing.

DESCRIPTION OF THE PREFERRED EMBODIMENTS

Figure 1:
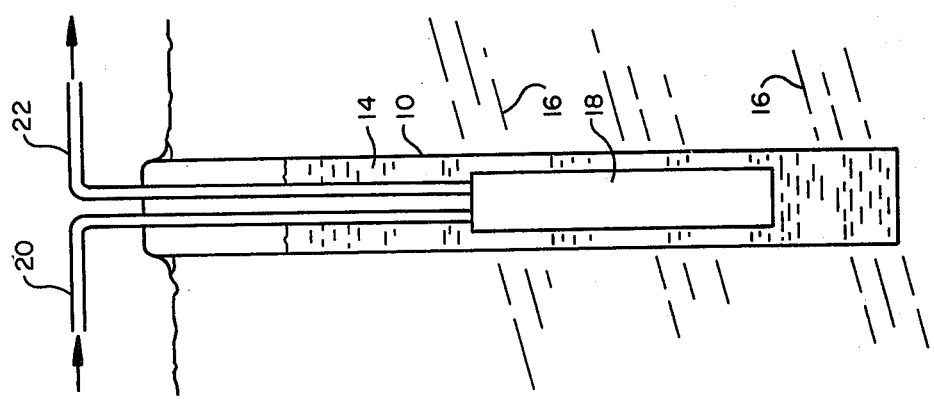
FIG. 1 is a plan view of the present invention.

Referring now to the drawing, FIG. 1 shows a simple embodiment of the present invention where the chemical reaction vessel is lowered into a geothermal well. A well head 12 is used to cap the well casing 10 at the surface of the ground. Well fluids 14 enter the well casing 10 from and circulate through rock fissures 16. A chemical reaction vessel 18 which contains a catalyst is suspended in the well fluids 14, which fluids heat the vessel. An inlet pipe 20 and a discharge pipe 22 pass through the well head 12 and lead reactant chemicals to and from the chemical reaction vessel 18.

Figure 2:
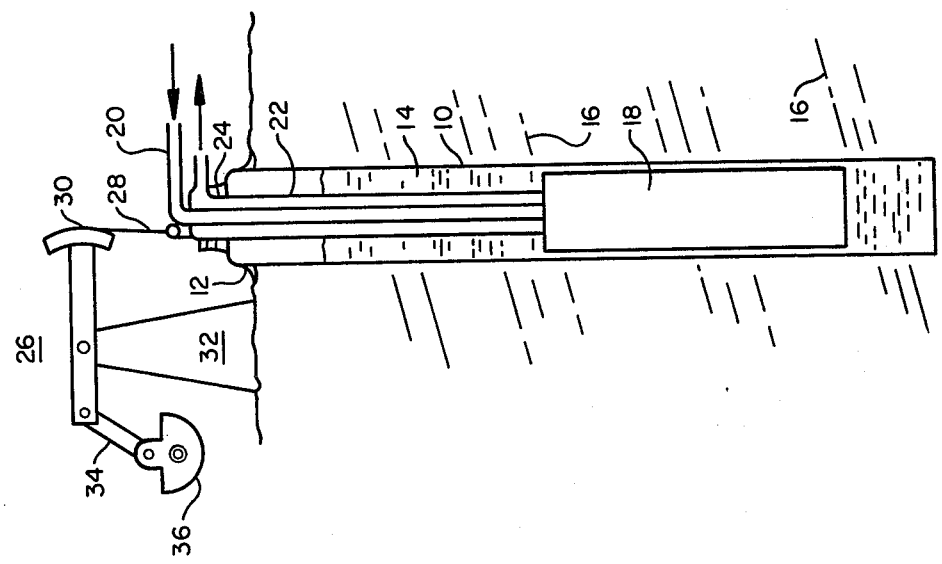
FIG. 2 is a plan view of still another embodiment of the present invention.

FIG. 2 shows a method of circulating the well fluids 14 around the chemical reaction vessel 18. A stuffing box 24 is situated in the well head 12 through which the input and discharge pipes 20 and 22, shown for convenience and practical application as two concentric pipes, pass. A well pump jack 26, having a connecting rod 28, a rocker arm 30 and base 32, and driven by a connecting rod 34, a crank 36 and a motor or other device (not shown), moves the chemical reaction vessel 18 with its associated input and discharge pipes 20 and 22 up and down, whereby the fluids 14 are effectively circulated around the chemical reaction vessel.

Figure 3:
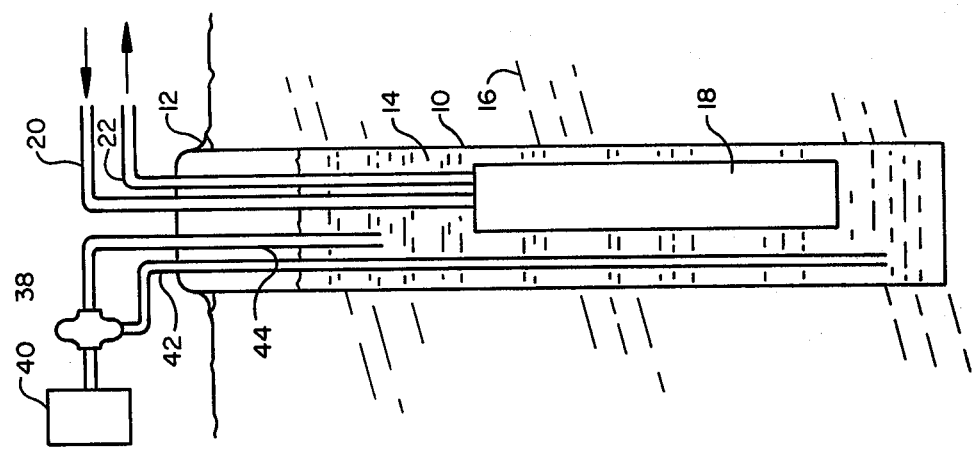
FIG. 3 is a plan view of still another embodiment of the present invention.

FIG. 3 shows an alternate method for circulating the well fluids 14 around the chemical reaction vessel 18. A pump 38, driven by a motor 40, is located as the well head 12. The pump 38 draws up well fluids 14 through a first pipe 42 and discharges the well fluids through a second pipe 44, establishing a net circulation past the chemical reaction vessel 18.

Figure 4:
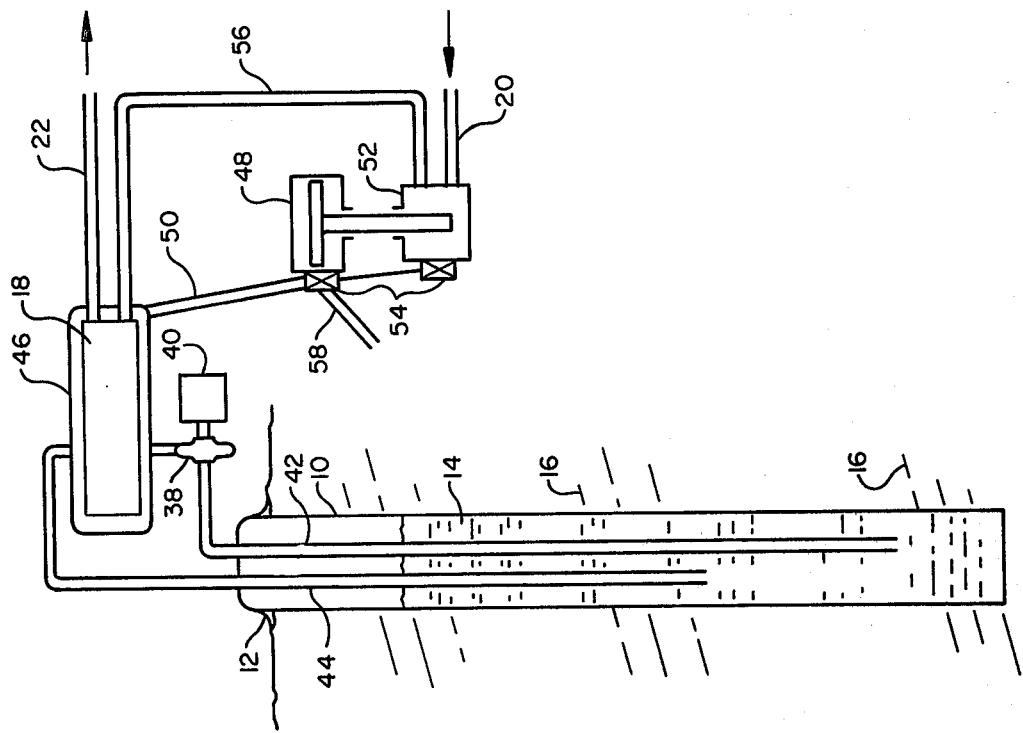
FIG. 4 is a plan view of yet another embodiment of the present invention.

FIG. 4 shows another embodiment of the present invention in the case where there is not a suitable temperature available in the geothermal well, or the source of geothermal energy is fluids emerging from the well. A jacket 46 surrounds the chemical reaction vessel 18 which is located above the ground. The pump 38, driven by motor 40, circulates the well fluid 14 up the first pipe 42, through the jacket 46, and back into the well through the second pipe 44.

Where the well fluids 14 are high pressure steams, the well fluids can be conveniently used to pressurize the chemical reactants in the chemical process, as shown further in FIG. 4. A second pump 48 uses a pressure tap 50 from the jacket 46 to compress the reactant chemicals in a high pressure cylinder 52. Valve boxes 54 control the operation of the second pump 48. The chemical reactants are fed to the second pump 48 through inlet pipe 20 and enter the chemical reaction vessel 18 through entry pipe 56. The flow of fluid which operates the second pump 48 must be discharged to atmosphere through exhaust pipe 58. This method for pressurizing the chemical reactants is not practical if the well fluids 14 are ecolgically harmful.

One chemical reaction which is well suited to the present invention is the catalytic conversion of carbon monoxide and hydrogen to methanol. This reaction takes place in the pressure range of 100–600 Atm and at temperatures from 250°–400° C, although where the temperatures are below 250° C there is still a reaction between dissolved carbon monoxide and hydrogen. The chemical reaction vessel 18 is lowered into a geothermal well of suitable temperature so it is immersed in the well fluid 14. The chemical reactants are fed to the chemical reaction vessel 18 under the necessary pressure to react with the catalyst within the chemical reaction vessel. The resulting product, such as methanol, is discharged through the discharge pipe 22 into any suitable container for storage and subsequent transportation to the use area. It is not necessary that there be a flow of fluid from the well, as a well drilled into hot rock would also be effective as long as there is effective thermal contact with the rock and the chemical reaction vessel 18. The thermal contact could be accomplished with uncirculated fluids. Also, since the pressure used in the chemical reaction is quite high, the external pressure of the fluids in a deep geothermal well lessens the design requirements of the chemical reaction vessel 18.

Where circulation of the well fluids 14 is desired for better energy flow and temperature, the chemical reaction vessel 18 can be "pumped" up and down as in FIG.

2, or a pump 38 can be installed as in FIGS. 3 and 4 to circulate the well fluid 14.

Finally, the chemical reaction can take place above ground by immersing the chemical reaction vessel 18 in the jacket 46 through which the well fluids 14 are pumped, as shown in FIG. 4. A portion of the well fluids 14 can be tapped to pressurize the chemical reactants where the fluids are under high pressure.

Other useful chemical reactions, such as the hydrogenation of carbon dioxide, since there is usually considerable carbon dioxide around geothermal sources, could be used. The measure of a suitable reaction is that the reaction absorb energy and be active at temperatures encountered in geothermal wells, and that the end product be a liquid at normal handling and storage temperatures. Other possibilities include ethyl alcohol and propyl alcohols with coal being gasified by heat and steam to provide the hydrogen-carbon monoxide feed for the alcohol synthesis. Obviously many other modifications and variations of the present invention are possible in light of the above teachings. It is therefore, to be understood that, within the scope of the appended claims, the invention may be practiced otherwise than as specifically described.

What is claimed is:

1. A method for using geothermal energy cmprising the steps of;
    immersing a chemical reaction vessel in which a chemical reaction which requires heat is to occur in a geothermal fluid having temperatures sufficient to maintain said chemical reaction;
    wherein the step of immersing comprises surrounding said chemical reaction vessel by a jacket and pumping said geothermal fluid through said jacket around said chemical reaction vessel;
    inputting the chemical reactants necessary for said chemical reaction to said chemical reaction vessel;
    pressurizing said chemical reactants from the natural pressure of said geothermal fluid; and
    discharging the end product of said chemical reaction from said chemical reaction vessel into a storage container.

2. A method for using geothermal energy as recited in claim 1 wherein said step of pressurizing comprises the steps of:
    tapping high pressure geothermal fluid from said jacket; and
    compressing said chemical reactants in a high pressure cylinder by using said high pressure geothermal fluid in a second pump.

* * * * *